United States Patent
Biglieri et al.

(10) Patent No.: US 7,042,219 B2
(45) Date of Patent: May 9, 2006

(54) METHOD FOR DETERMINING THE CONDITION OF AN OBJECT BY MAGNETIC RESONANCE IMAGING

(75) Inventors: Eugenio Biglieri, Masio (IT); Luigi Satragno, Genova (IT)

(73) Assignee: Esaote S.p.A., Casale Monferrator (IT)

( * ) Notice: Subject to any disclaimer, the term of this patent is extended or adjusted under 35 U.S.C. 154(b) by 65 days.

(21) Appl. No.: 10/916,406

(22) Filed: Aug. 12, 2004

(65) Prior Publication Data

US 2006/0033493 A1 Feb. 16, 2006

(51) Int. Cl.
*G01V 3/00* (2006.01)

(52) U.S. Cl. .................. 324/309; 600/410

(58) Field of Classification Search .......... 324/309, 324/307, 300; 600/410
See application file for complete search history.

(56) References Cited

U.S. PATENT DOCUMENTS

| | | | |
|---|---|---|---|
| 4,674,110 A | 6/1987 | Eaton et al. | |
| 5,262,945 A * | 11/1993 | DeCarli et al. | 600/410 |
| 5,657,369 A | 8/1997 | Stein et al. | |
| 5,734,739 A * | 3/1998 | Sheehan et al. | 382/128 |
| 6,459,927 B1 | 10/2002 | Franklin et al. | |
| 6,681,132 B1 * | 1/2004 | Katz et al. | 600/410 |
| 6,799,066 B1 * | 9/2004 | Steines et al. | 600/407 |
| 6,819,952 B1 * | 11/2004 | Pfefferbaum et al. | 600/410 |
| 2002/0077539 A1 | 6/2002 | Schmit et al. | |
| 2002/0103428 A1 | 8/2002 | deCharms | |

FOREIGN PATENT DOCUMENTS

| | | |
|---|---|---|
| EP | 0 930 510 A2 | 7/1999 |
| WO | 79/00779 A1 | 10/1979 |
| WO | 02/22013 A1 | 3/2002 |

OTHER PUBLICATIONS

European Standard Search Report, Apr. 28, 2004.
E. Mark Haacke et al., Magnetic Resonance Imaging, Physical Principles and Sequence Design, 1999, pp. 194-195, Wiley-Liss, A John Wiley & Sons Inc. Publication, New York.
M.A. Foster et al., "Practical NMR Imaging," 1987, IRL Press, UK.
Hemmendorf, M. et al., "Phase-based multidimensional volume registration," IEEE Trans Med Imaging 2002, pp. 1536-1543, vol. 21.

* cited by examiner

Primary Examiner—Louis Arana
(74) Attorney, Agent, or Firm—Buchanan Ingersoll PC

(57) ABSTRACT

A method for determining the condition of an animate or inanimate object by magnetic resonance imaging, MRI, particularly for determining the pathologic condition of rheumatoid arthritis ("arthritis rheumatoides") and carrying out a patient follow-up.

53 Claims, 6 Drawing Sheets

SAMPLE OBJECTS OF KNOWN CONDITION

| Sample Objects | Functions | Known Condition |
|---|---|---|
| 1 | f1 | C1 |
| 2 | f2 | C2 |
| 3 | f3 | C3 |
| N | fn | Cn |

| Sample Objects | Functions Parameter | Known Condition |
|---|---|---|
| 1 | P(f1) | C1 |
| 2 | P(f2) | C2 |
| 3 | P(f3) | C3 |
| N | P(fn) | Cn |

OBJECT OF UNKNOWN CONDITION TO BE DETERMINED

| Object to examine | Function | Known Condition |
|---|---|---|
| E | fE | unknown |

| Object to examine | Function Parameter | Known Condition |
|---|---|---|
| E | P(fE) | unknown |

Comparison

COMPUTED CONDITION OF EXAMINED OBJECT

METHOD FOR DETERMINING THE CONDITION OF AN OBJECT BY MAGNETIC RESONANCE IMAGING

FIELD OF THE INVENTION

The present invention relates to a method for determining the condition of an animate or an inanimate object by MRI.

BACKGROUND OF THE INVENTION

The present invention particularly relates to a method for determining the condition of an animate or an inanimate object which condition can be evaluated by providing information on time dependent effects which are either induced or spontaneous. For example, in a solid body which is not of a biological type, the perfusion of a gas or a liquid which is fed under certain condition can be observed by MRI, such as by acquiring a sequence of images in which each image is acquired at a different time within a certain time period. Structural modifications relating to a change in physical or chemical parameters can be observed, such as, for example, temperature dependent structural changes in solid bodies which are subjected to temperature which varies over time by heating or by cooling or structural changes which are induced by mechanical stress that is exerted on a body, or structural or chemical changes that are induced by exposure to radiation in which the intensity or dosage changes with time, structural or chemical changes which occur due to the application of chemical substances to the body that are interacting with the substance or the material of which the body is made.

Such time dependent effects may be observed by carrying out an MRI session of the body in which an image is acquired at predetermined time intervals. In this way, the time dependent changes in parameters of the image may be empirically determined, for example, time dependent changes of the mean intensity of the image or of only a partial area of the image.

In many cases, particularly in cases in which MRI is applied for diagnostic purposes, the pathological condition of in vitro or living tissues is a time dependent activity or one which can be best appreciated by using induced mechanisms in the tissue which are time dependent. This means that in order to isolate or to identify the condition of the object it is necessary or preferable to carry out a sequence of images, with each image being acquired at certain different times within a certain time interval.

Particularly relevant is the case for isolating and identifying and evaluating pathologic conditions such as infections and/or tumors, or the like. It is known that vascularisation is enhanced in regions in which tumoral cells are present or in which there is an infection. Thus in this case in order to isolate and identify such conditions it is known to evaluate the increase of vascularisation by means of contrast media perfusion measurements.

Perfusion measurements conducted with MRI are usually carried out by acquiring a sequence of images of a selected anatomical region or tissue region after a contrast media has been injected into the region. Contrast media are transported by the blood and the speed of transport of diffusion of the contrast media in the tissue or anatomical region of interest is used for evaluating vascularisation. The mean intensity of the imaged region of interest is then determined from the image data of each image of the sequence and a so-called "perfusion curve" is constructed from the data pairs, the mean intensity of the region of interest of each one of the images of the sequence of images, and the time of acquisition of the images.

By comparing the perfusion curve with other perfusion curves which are uniquely related to known clinic cases or tissue conditions, it is then possible to determine some indications on the clinical condition of the imaged tissue or anatomical region.

This evaluation has been carried out until now in a non-systematic way.

Thus there is the need for providing for a method of determining a condition of an object, particularly the pathological condition of living or in vitro tissues which is much more reliable and which is integrated in a well defined manner and which automatically determines the indications about the probable pathological condition of an object under examination which pathological condition is unknown.

The invention therefore has the aim of providing a method for determining the condition of an object by MRI.

The invention is directed to providing a method enabling one to have unique criteria so that measurements carried out by different subjects and different devices can be reliable and comparable, thus permitting a widespread exchange of data between different subjects which carry out the examination and evaluate the results.

Another goal of the present invention is to reduce the uncertainties related to the skill involved in carrying out such examinations and in visually comparing and interpreting the results.

SUMMARY OF THE INVENTION

The above mentioned goal is achieved by the method the present invention for determining the condition of an object by MRI, comprising the following steps:
a) acquiring at least one image of a sample object by MRI along at least one slice or one section plane of an object under examination at different successive times within a predetermined time period;
b) the sample object having known conditions;
c) determining for each image or for a selected region of each image, which selected region is identical for each image or refers to an identical part of the imaged sample object under examination, the mean intensity of the MRI signal;
d) constructing an empirical time dependency function of the mean intensity by using data pairs consisting of the mean intensity of each image or of the part of each image and the corresponding time of acquisition;
e) analytically determining the parameter of a function approximating the said empirical time dependency function;
f) providing at least a second object to be examined having an unknown condition and carrying out the steps a) to e) using the second object; and,
g) comparing the parameters of the function which approximates the empirical time dependency function relating to the sample object with the parameters of the second object in order to detect differences of the condition of the second object from the known conditions of the sample object.

Objects being examined which are either of a biological or a non-biological type and/or which are inanimate or animate are often of the type which are able to show at least two or more conditions or a continuously varying range of conditions. In this case, the above mentioned steps may be carried out for every discrete possible condition of the body under examination or for only a certain number of different selected conditions of the continuously varying conditions.

The unknown condition of additional objects may be determined by carrying out the steps described in the precedent paragraph for these additional objects and then comparing the parameters of the function approximating the empirical time dependency function relating to the additional objects with the parameters of the function approximating the empirical time dependency function relating to the sample object(s).

Different mathematical or statistical tools may be applied for carrying out the comparison of the parameters of the function approximating the empirical time dependency function relating to additional objects with the parameters of the function approximating the empirical time dependency function, i.e. in order to determine the condition of the examined objects, which condition is unknown. Having a range of discrete conditions relating to the sample objects, the condition of the object under examination may be determined by interpolation. A different approach may consist of generating a database comprising time dependent functions of the sample objects relating to their condition and to the corresponding known condition and using a predictive algorithm such as a neural network for determining the condition of the object under examination on the basis of the time dependent mean intensity function obtained by acquiring the sequence of MRI images.

When the objects do not show time varying effects which produce time varying image parameters, particularly to time varying intensities of the images of the sequence of MRI images, the time varying parameters can be induced or forced by applying to the sample objects and to the additional objects (for which the condition has to be determined) a medium which is able to diffuse within the objects and then carrying out the acquisition steps of one or more images of the objects along one or more selected slices or section planes within a time period starting before or at or immediately after the application of the diffusion media and ending after the complete diffusion of the media in the object.

In order to select the slice or slices along which the sequence of images has to be acquired, a first panoramic image (a so-called "scout image") is acquired along a first scout slice or section plane by which one or a series of selected section planes across the objects are determined and along each of which an image has to be acquired.

Furthermore, when only a limited and known region of the images along the selected slice or slices has to be examined or is relevant for determining the condition, a first image along a first section plane is acquired and then the limited region of the image is determined (which region is a so-called "region of interest" or "ROI"), the geometric shape and position of the region of interest being determined and selected on each further image which is acquired at later times along the same slice or section plane.

Determining the region of interest is particularly relevant in the case in which the object to be examined is an anatomical region of a patient, either human or animal.

The present invention can be further improved by noting that instead of acquiring images along one or more section planes or slices, a three-dimensional image of the sample objects and of the objects having unknown conditions (or of a part thereof) may be acquired, thus collecting a sequence of three-dimensional images which are each acquired at different times within a certain time period.

Acquiring a sequence of three-dimensional images which can be stored as volumetric image data allows one to define and select section planes and regions of interests at a later time, without running the risk of having to repeat the acquisition process due to an imprecise or incorrect selection of the slices and/or of the regions of interest.

After having acquired the sequence of three-dimensional MRI images or alternatively in the acquisition process in a first three-dimensional image, one or more three-dimensional partial regions are selected, said regions being so-called three dimensional regions of interest, and the position in space and boundaries of the regions of interest being determined, while the regions of interest are automatically selected for each subsequent three-dimensional image being acquired at later times, the mean intensity of the image data of each three-dimensional region of interest being calculated from the image data and used for constructing an empirical time dependency function of the mean intensity of the region of interest by the data pairs consisting of the mean intensity of each three-dimensional region of interest of each three-dimensional image of the sequence of three-dimensional images and the corresponding time of acquisition.

It is also possible not to limit examination to only one region of interest. In this case, two or more selected regions of the sequence of two-dimensional images along one or more selected slices or section planes of the objects or of the sequence of three-dimensional images of the objects are defined and an empirical time dependency function of the mean intensity is constructed separately for each different selected region by the data pairs consisting of the mean intensity of the corresponding selected region of each corresponding two- or three-dimensional image of the sequence of two- or three-dimensional images and the corresponding time of acquisition.

A further alternative or improvement consists in the fact that two or more selected regions of the sequence of two-dimensional images along one or more selected slices or section planes of the objects or of the sequence of three-dimensional images of the objects are defined and an empirical time dependency function of the mean intensity is constructed in which for each two-dimensional image along one selected plane or section plane of the sequence of section planes or for each three-dimensional image of the sequence of three-dimensional images the mean intensity is determined by the sum of the mean intensities of the different selected region of interests.

When limiting imaging to the two-dimensional case, the images along one or more selected slices or section planes are acquired through a three-dimensional image of the objects;

defining within the three-dimensional image one or more planes crossing the volume represented by the three-dimensional image; and, reconstructing the image along the one or more planes from the three-dimensional image data by selecting the image data falling on each selected plane crossing the volume.

In order to have comparable data from different objects examined, it is important that the region of interest being chosen corresponds to the identical region of the real object. In the case of diagnostic images, this means that the region of interest for each object should correspond to the same anatomical region for each object and sample object being examined. In order to ensure this, the invention provides markers which are applied to the objects in uniquely defined positions, with the markers generating uniquely recognizable image data in the images being acquired and with the selected region or regions being defined by the geometrical relation of the markers with the position and boundaries of the selected regions.

As an alternative to external markers which are positioned in well defined points of the object, markers can also be used which are defined as selected zones or regions of the objects which are uniquely identifiable in the images of the selected slices or section planes or in the three-dimensional images.

For each slice image of the sequences of slice images or for each three-dimensional image of the sequence of three-dimensional images, the selected region of interest or the selected regions of interest may be uniquely identified by their known geometrical form and from the geometrical relation (distance and orientation) relative to the markers. This operation can be carried out by use of a simple mathematical algorithm such as, for example, a so-called "registration algorithm" which is well known in the art (see for example Hemmendorf, M.; Anderson, M. T.; Kronander, T.; Knutsson, H. Phase-based multidimensional volume registration, IEE Trans Med Imaging 2002, 21, 1536–43).

A particular field of use of the above-mentioned invention is the field of diagnostic imaging. The above method can be used for determining whether, on the basis of MRI images of an anatomical region of a patient, a pathological condition is present in that region and, if it is present, the above-mentioned method can provide as a further improvement also an evaluation of the level or stage of the pathological condition.

Particularly in the case of infections and/or of tumors, the present invention comprises carrying out the method by acquiring a sequence of images of the anatomical region, which images are taken at certain times during a certain period with that period lasting long enough to allow a complete perfusion of the anatomical region by a contrast media which is injected in that anatomical region.

A particular kind of disease or illness suitable for examination using the present invention could be rheumatoid arthritis (or "arthritis rheumatoides"). As an important region of interest to which imaging has to be carried out, the sinovial can be used. It has been shown that this anatomical region is representative for identifying the stage or level of activity of the disease.

Furthermore the invention can be used for carrying out a follow-up, thus helping to recognize the way that the pathological condition develops or the way that the said pathological condition is regressing due, for example, to medical treatment.

Thus, for the above purposes, the invention relates to a method for carrying out a follow-up of the pathological conditions of biological tissues in isolated form or in or of an anatomical region of a body comprising the steps of:
a) acquiring at least one image by MRI along at least one slice or along one section plane or a volume or a selected three-dimensional region within the volume of the biological tissue(s) having a known condition at different successive times within a predetermined time period;
b) determining the mean intensity of the MRI signal for each image or for a selected region of each image, which selected region is identical for each image or refers to an identical part of the imaged sample biological tissue(s) under examination;
c) constructing an empirical time dependency function of the mean intensity by using the data pairs consisting of the mean intensity of each image or of the part of each image and the corresponding time of acquisition;
d) analytically determining the parameter of a function approximating the empirical time dependency function;
e) providing at least a second biological tissue to be examined having an unknown condition and carrying out the steps a) to d) using the said second biological tissue;
f) comparing the parameters of the function approximating the empirical time dependency function relating to the sample biological tissue(s) and to the second biological tissue(s) having an unknown condition in order to detect differences of the condition of the second object from the known conditions of the sample object.

Considering the use of the present invention for a follow-up of the disease, the invention has the following steps:
repetition, at several different times, of the steps e) and f) for determining changes in the degree of disease activity over time and during a therapeutic treatment.

When the above method is applied in combination with the presence of contrast media in the examined object or in the region of interest of the examined object, the follow-up of the disease activity of a pathological condition of the object and within the region of interest comprises the steps of:
a) generating a database of contrast media perfusion curves each one uniquely associated to a well-defined degree of disease activity;
b) the database being generated by acquiring at least one image of an identical region of interest of the same anatomical region by MRI along at least one slice or one section plane of the anatomical region in patients or a three-dimensional MRI image of the anatomical region in more than one patient, each patient having a known degree of disease activity;
c) for each patient having a well-defined degree of disease activity, acquiring a sequence of MRI images which sequence comprises a certain number of MRI images taken at different times, one from the other, within a certain period of time;
d) the period of time starting immediately after or at the injection of a contrast medium in the anatomical region and terminating after a certain time which is determined as a typical duration of contrast media perfusion in the anatomical region;
e) determining for each image or for a selected region of each image, which selected region is identical for each image or refers to an identical part of the imaged anatomical region under examination, the mean intensity of the acquired image data;
f) constructing an empirical time dependency function of the mean intensity by using the data pairs consisting of the mean intensity of each image or of the part of each image and the corresponding time of acquisition;
g) analytically determining the parameter of a function approximating the empirical time dependency function;
h) determining the disease activity in the same region of interest of the same anatomical region of a patient having an unknown level of disease activity by carrying out the steps of injecting the contrast media in the anatomical region of the patient and by acquiring the sequence of MRI images of the anatomical region for the predetermined period of time and finally constructing the empirical time dependency function of the mean intensity by using the data pairs consisting of the mean intensity of each image or of the part of each image and the corresponding time of acquisition and analytically determining the parameter of a function approximating the empirical time dependency function;
i) comparing the parameters of the function approximating the empirical time dependency function relating to the database in order to detect the disease activity level; and, j) repeating at several different times the steps h) and i) for determining changes in the degree of disease activity over time and/or during a therapeutic treatment.

The above mentioned method allows one to estimate the health condition of a patient and the time development of disease with or without therapy.

It has been found that the above mentioned method allows one to determine the level of disease activity and the health condition of rheumatoid arthritis in patients by MRI perfusion measurements of the wrist and particularly of the synovial membrane. Indeed, the synovial membrane is the anatomical site where early inflammation can be detected. The method allows one to discriminate an active disease from an inactive disease and the level of activity.

In this case, the anatomical region under examination is the wrist and the region of interest is the synovial membrane.

Since the measurements relate to determining a mean intensity of the image along a selected region which is the entire region of interest or a selected part thereof and since the follow-up requires that imaging has to be carried out in different sessions at different times, it is important and critical that at each session the same slice or region of interest is selected. This can be very difficult to perform and can provide errors since the correct selection depends on the positioning of the wrist in the MRI scanner. Thus, using a three-dimensional MRI acquisition method and considering the mean intensity of an entire three-dimensional region of interest or of a three-dimensional part thereof, can be helpful in avoiding errors due to improper positioning and thus to the selection of an incorrect section plane or an incorrect region of interest. Further providing markers either of the external kind or consisting in precise anatomical or morphological particulars of the anatomical region under examination, and combining the markers with the above-mentioned registration methods and algorithms allows one to enhance the precision of the method also in combination with the three-dimensional MRI acquisition.

Further improvements of the present invention are described in the dependent claims.

BRIEF DESCRIPTION OF THE DRAWING FIGURES

The present invention and the advantages deriving therefrom will appear more clearly from the following description of some illustrative examples and of the annexed drawings and tables, in which.

It is to be stressed that while the examples on which the following description is based relate to a biological case in which the object under examination is the wrist of a living patient, the method is not limited to this example.

Examinations of the same kind can be carried out on animate and inanimate bodies or on in vitro tissues. Furthermore, the present method can be applied at least relatively to its basic steps on non-biological objects. For example, on inanimate materials, where instead of the so-called contrast media, the perfusion or transition of waves or of fluids such as liquids or gas or particles modifying their structure may be used, especially where the modifications induced by the said media are visible by MRI.

DETAILED DESCRIPTION OF THE INVENTION

Figure 1:
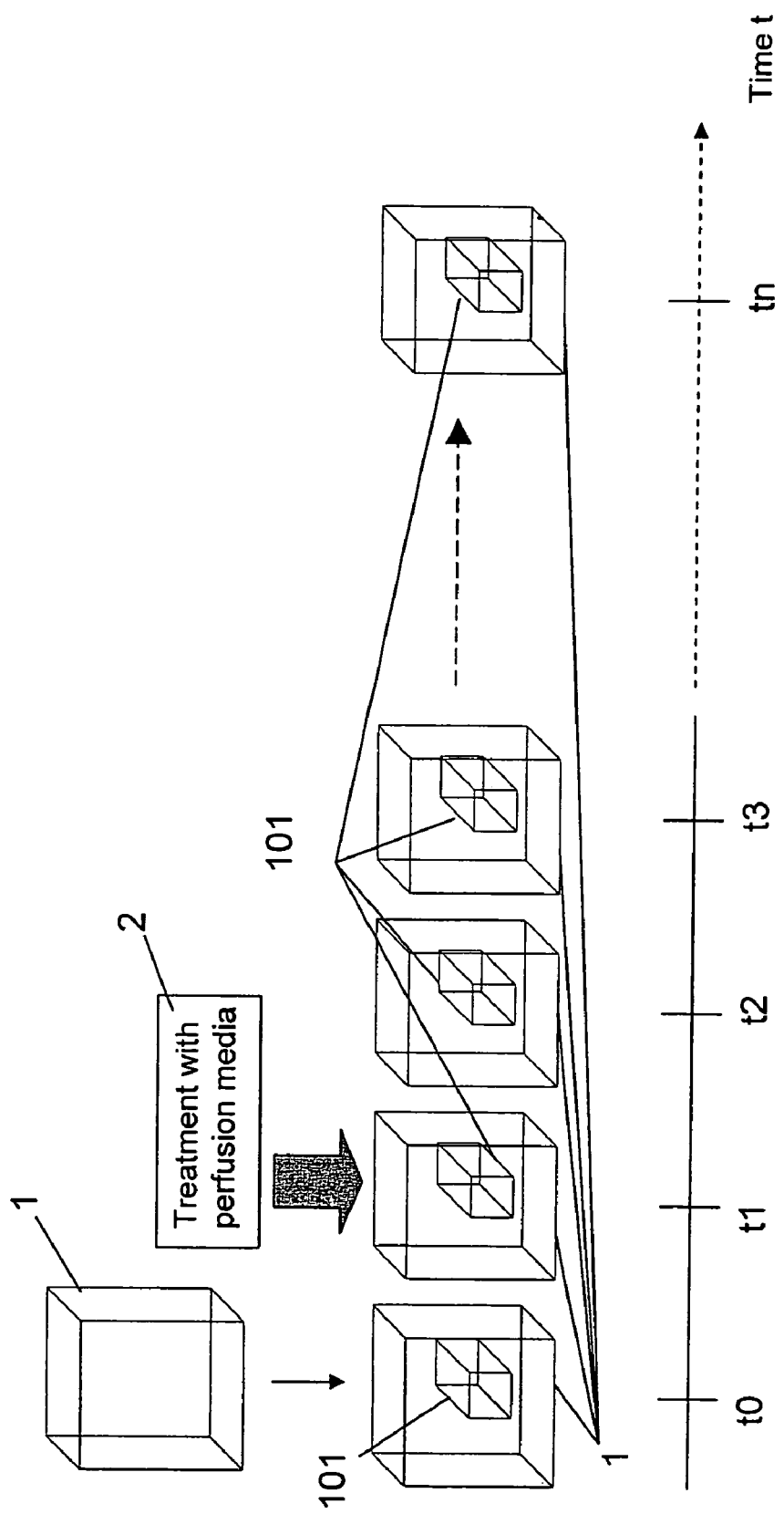
FIG. 1 shows a diagram explaining the basic steps of the method according to the present invention relative to the sequence of MRI acquisitions carried out for a contrast media perfusion measurement and relative to the case using three-dimensional MRI.

Relating to FIG. 1, an object 1 is represented by a cube. The object 1 is positioned in an MRI scanner and one or more panoramic images are acquired, the so-called "scout images". If needed, these images are used by the operator to select a certain particular region of the object 1, a so-called "region of interest" (ROI) indicated by a small cube 101 within the object 1.

Thus, the apparatus is ready to carry out a sequence of images of the same region of interest 101 at different times.

FIG. 1 illustrates the sequence of imaging acquisitions along a time axis t by reproducing the image of the object 1 and of the region of interest 101 at each acquisition time ti, where i=0, 1, 2, 3, . . . , n.

The object 1 under examination can show spontaneous time varying states which are typical for a certain condition of the object. If this is not the case, a time varying state can be induced in the object under examination 1 and more precisely in the region of interest by subjecting the object to a treatment. Such treatment can be, for example, the injection of a fluid such as a gas or a liquid which is able to permeate the body under examination or the application of a mechanical wave or of an electric or electromagnetic wave or signal.

A typical case in the examination of biological tissues is the injection of contrast media. This is indicated schematically by the reference numeral 2 in FIG. 1. Contrast media are transported by the vascular or lymphatic system and their concentration varies over time from the instant of injection. Contrast media are known and give a very high and identifiable MRI signal. By repeating the MRI image acquisition several times at different times from injection of the contrast media in the object under examination, the quantity of contrast media in the region of interest 101 first increases and then roughly reaches a maximum which is maintained for a certain time. In the MRI images of the sequence, this can be detected by examining the mean intensity of each image of the sequence. Reporting these values in relation to the time of acquisition, allows one to draw a so-called perfusion curve, an example of which is illustrated on FIG. 2. The stars indicate the measured values of the mean intensity of each MRI image of the region of interest 101 at the time of their acquisition. The curve passing through the stars is an interpolation curve which represents a function of the mean intensity with respect to time.

These kinds of measurements are known as perfusion measurements and are used in MRI diagnostic and in ultrasound diagnostic.

In diagnostic use, perfusion curves give a measure of vascularisation of a tissue or anatomical region which is a sign of the presence of an abnormal condition. Increased vascularisation can be observed in the presence of inflammations, infections and also tumors. Thus perfusion measurements can be of help in determining a pathological condition of a patient.

If non-biological material is considered, such as, for example, permeable materials, then a fluid or a gas can be applied with a certain pressure to the permeable material and then the perfusion curve of the fluid can be determined in order to evaluate the homogeneity of permeation within the entire cross section and length of the material and/or whether the permeability has to follow a certain direction of flux deviations, can be observed.

Figure 3:
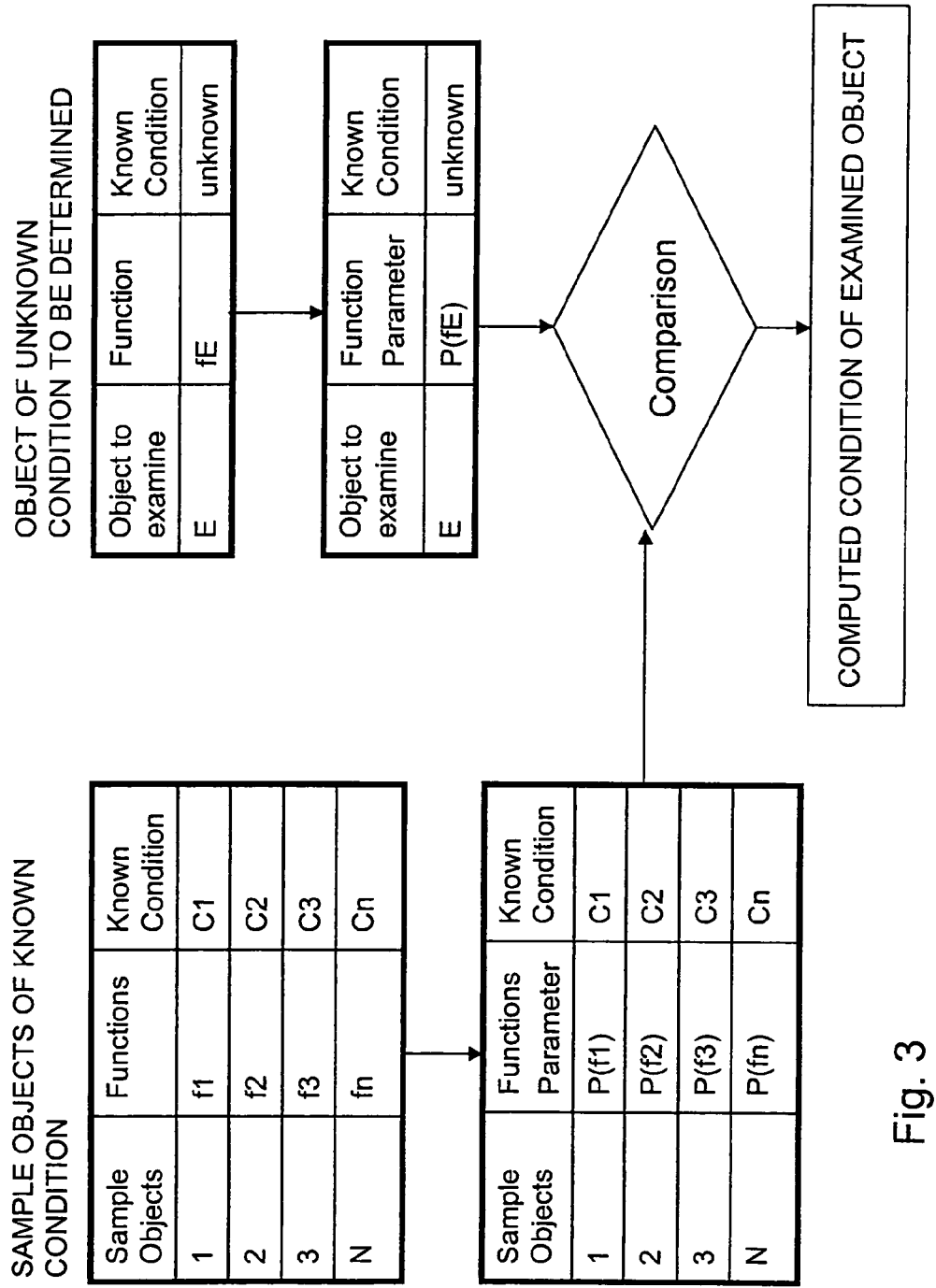
FIG. 3 is a table in the form of a flux diagram explaining the method steps of the invention according to a first embodiment.

In order to be able to evaluate the condition of an object by the method according to the present invention, a certain number of sample objects having a known condition have to be submitted to the perfusion measurements, as indicated by the diagram of FIG. 3. In this case, perfusion measurements according to the above description are carried out for each of the n sample objects and the so determined empirical perfusion functions f1 to fn are determined. These functions can be uniquely related to the known conditions C1 to Cn of each of the said n sample objects.

Each empirical function f1 to fn can then be approximated by a function as, for example, a polynomial expansion or series in which parameters P(f1) to P(fn) are uniquely correlated to the conditions C1 to Cn of the said n sample objects. Algorithms which are capable of carrying out this step are known and widely used by persons skilled in the art, since the algorithms are within the common, general knowledge.

Thus a database has been constructed which comprises data vectors consisting of the parameters P(f1) to P(fn) and the corresponding condition for the sample object.

The database further comprises the definition of the region of interest 101 which is the same for each sample object and which corresponds to the same part in each sample object.

The method according to the present invention further provides the steps of carrying out the perfusion measurement of the same region of interest 101 which is located at the same part of an object to be examined regarding an unknown condition. This is shown at the left column of FIG. 3.

Figure 2:
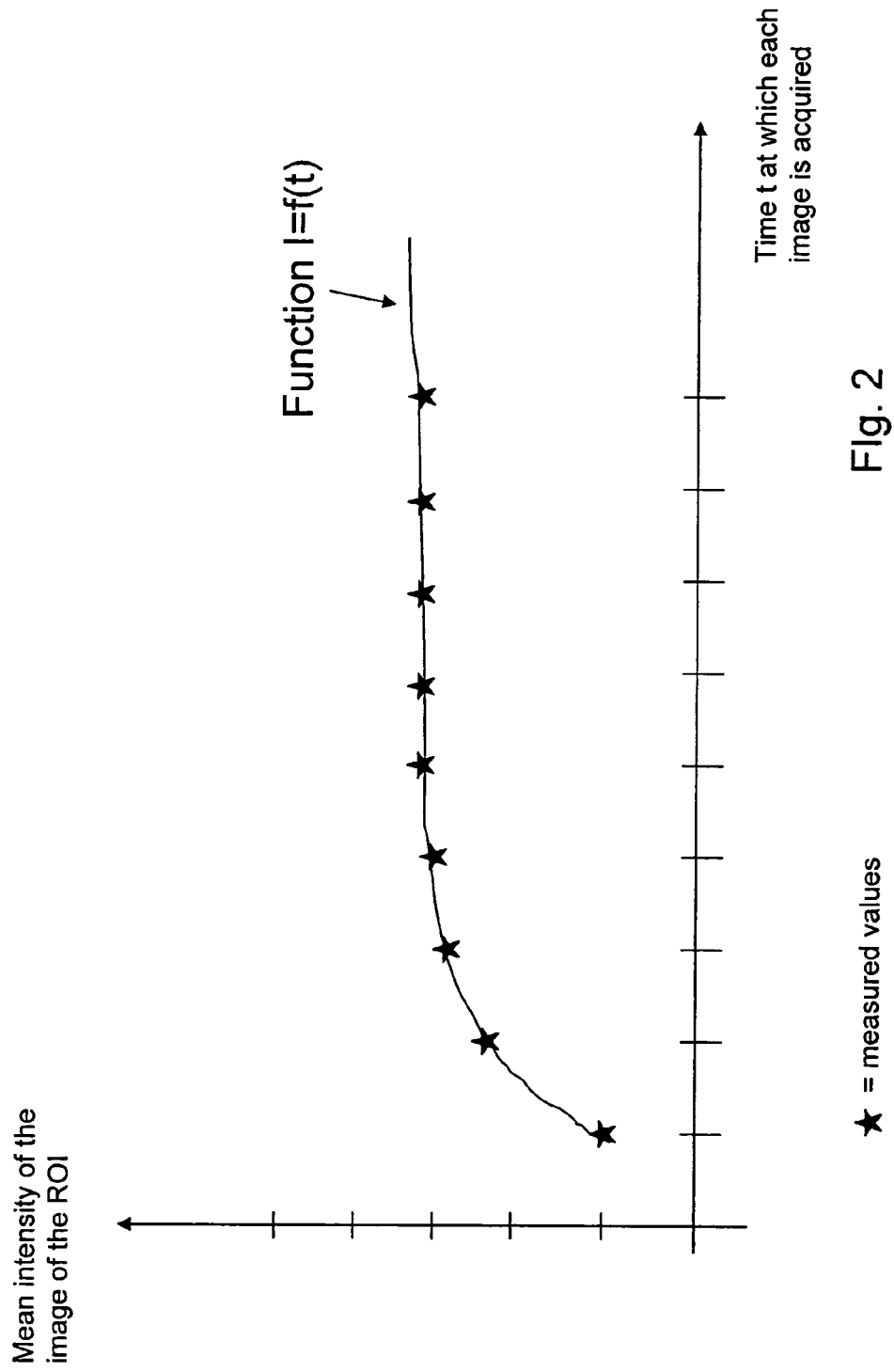
FIG. 2 shows an example of a typical perfusion curve obtained by reporting the mean intensity of the region of interest of images taken at different times with respect to the time of acquisition.

Imaging and the determination of the perfusion curve fE and the determination therefrom of the parameters P(fE) is carried out in exactly the same manner as disclosed above for the sample objects and with reference to FIGS. 1 and 2.

A comparison step of the parameters P(fE) with the database allows one to identify at least the closest condition C1 to Cn to which the condition CE of the object under examination for an unknown condition exists. Different cases may be possible. If one considers that the objects may have only discrete conditions, then no interpolation is necessary. If the conditions of the objects may vary continuously, then the condition of the examined object having an unknown condition may be further determined by interpolation when the parameters P(fE) falls between two parameters of the sample objects.

Also when carrying out MRI of the object under examination for an unknown condition, it is important to determine the same region of interest 101 located at the same part of the object as in the sample objects.

Although the present invention can be carried out considering imaging along one or more selected slices, i.e., section planes of the objects, thus being limited to a so-called two-dimensional MRI case. The best results can typically be achieved by using three-dimensional MRI.

Three-dimensional imaging techniques are known and allow one to acquire a three-dimensional array of image data. (See, for example, "Magnetic Resonance Imaging, Physical Principles and Sequence Design" E. Mark Haacke, Robert W. Brown, Michael R. Thompson, Ramesh Venkatesan John Wiley & Sons Inc. Publication,; "Practical NMR Imaging" M. A Foster & J. M. S. Hutchinson IRL Press). In this case, uncertainty, relating to the fact that for each object the same slice or slices or the same section plane or section planes are selected due to different positioning of the objects relative to the MRI scanner, is widely reduced.

Three-dimensional MRI allows one also to carry out the method by using slice images, since once a three-dimensional image data array has been acquired. A section plane or slice of the imaged volume can be defined and the image data falling on the said slice can be selected and retrieved from the image data memory.

Nevertheless, as said above, choosing to use a three-dimensional region of interest 101 allows one to improve precision.

In order to further enhance precision, either in the case of two-dimensional MRI or of three-dimensional MRI, markers can be provided on the objects under examination.

These markers can be external markers which are applied on the objects at the same places relative to the shape of the objects. This can be done by identifying morphologically or anatomically unique points on the objects surface.

Markers provide for uniquely identifiable MRI signals which can be used to bring into register the images acquired from each different object. Register algorithms capable of carrying out this task are known. One such algorithm and the corresponding method are disclosed in Hemmendorf, M.; Anderson, M. T.; Kronander, T.; Knutsson, H. Phase-based multidimensional volume registration. EE Trans Med Imaging 2002, 21, 1536–43.

FIGS. 6A to 6D explain, with a simplified example, the effects of such combination of markers and registration algorithms.

FIGS. 6A to 6D show schematic views of different MRI sessions carried out at different times. Each time positions the object, which in this case is a hand, in the scanner and each time defines an imaging volume enclosing the hand. Markers are provided at selected identical positions on the hand for carrying out a slice image registration in order to identify at each imaging session the same section plane across the hand along which a slice image has to acquired and displayed.

In FIGS. 6A to 6D, the volume V defined by the user and in which the image data has to be acquired is represented by a rectangle. Assuming, for simplicity, that this volume is always the same at each imaging session, the hand can be positioned differently at each session relative to the volume with respect to all the other sessions. Thus, section plane P1A, defined in the session represented by FIG. 6A, will correspond if referred to the hand as a body under examination to section plane P1B, P1C and P1D in the following imaging sessions represented by FIGS. 6B to 6D.

In order to identify the correct section plane, at least one and preferably two or more markers can be provided. The markers can be, as illustrated in FIGS. 6A to 6D, MRI opaque elements 30 which can be positioned on the body under examination at uniquely and repeatedly identifiable points of the anatomy or shape of the body.

Alternatively, the markers can be parts or zones of the anatomy of the body under examination which are uniquely recognizable as particularly evident zones and which are constant. This allows one to use these zones as intrinsic markers.

Combination of these anatomic markers and of the opaque elements can also be used.

The example is referred to the identification of a section plane within a volumetric image data but the same method applies also when a three-dimensional region of interest 101 has to be identified and correctly oriented relative to the object to be imaged.

The markers can be searched and identified within each of the volumetric image data acquired at each imaging session. The markers can be used to spatially align the volumetric image data of a predefined region of interest 101 by applying a so-called "registering algorithm" as discussed above.

Figure 6:
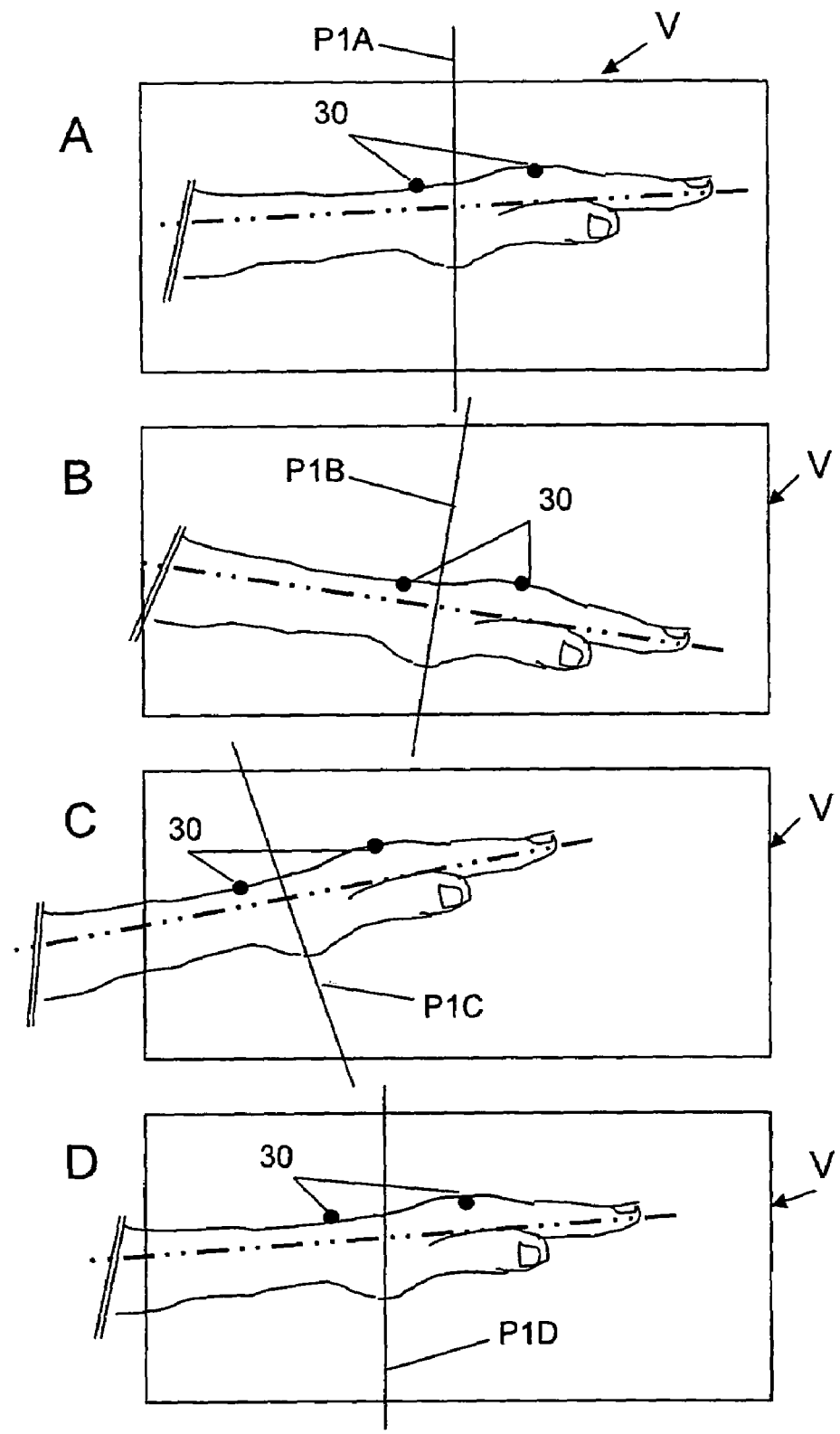

The effect of the registration algorithm is that, referring to the example of FIGS. 6A to 6D, the plane P1A can be correctly repositioned relative to the imaged object (namely the hand) in the image data of subsequent imaging sessions by giving to it the correct orientation as indicated by P1B, P1C, P1D in FIG. 6B, 6C, 6D. The same applies in the case of a volumetric region of interest 101.

The position of the object to be imaged, namely the hand, can be identified and displacement vectors can be determined with reference to the position of the hand in FIG. 6A, which displacement vectors can be used by calculating the new position and orientation parameters of the section plane, such as the section plane P1A of the illustrated example, or of a volumetric region of interest 101 relative to the different positions of the hand in each of the subsequent imaging sessions.

Thus, for each imaging session, the same section plane or volumetric region of interest can be identified allowing one to carry out reliable comparisons between the acquired image data.

Figure 4:
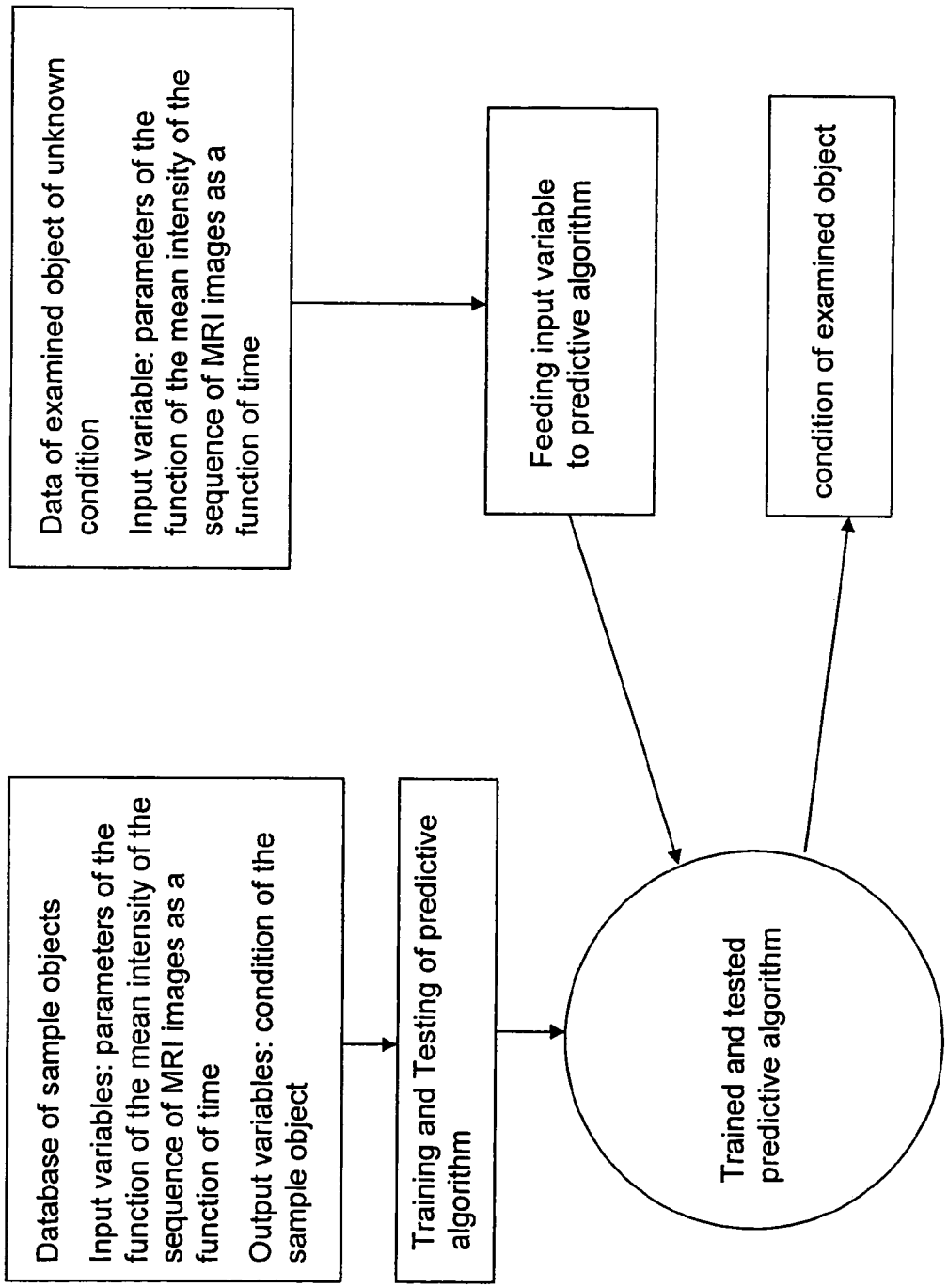
FIG. 4 is a variant of the embodiment according to FIG. 3 where a predictive algorithm is used for evaluating the condition of the examined object.

FIG. 4 illustrates a variation of the method according to FIG. 3.

In this case, the same database as in FIG. 3 is used, namely a database comprising as input variables the parameters P(f1) to P(fn) of the functions f1 to fn of the mean intensity of the sequence of MRI images as a function of time of each of the n sample objects. The output variables are the uniquely correlated conditions C1 to Cn of each one of the sample objects.

This database is used for training and testing a predictive algorithm, such as an artificial neural network. The data of the examined object for which a condition CE is unknown, namely the parameters P(fE) of the function fE of the examined object, are provided to the trained and tested predictive algorithm and the algorithm then determines the condition of the examined object. In this case, the determination of the condition of the object is not carried out using a simple comparison, but instead using the more sophisticated predictive algorithm.

The fact that the method according to the invention allows one to determine a condition of an examined object based on MRI image acquisitions of sample objects, and the combination of the method with the marking and registering steps and with a three-dimensional MRI image acquisition technique, ensures that the results are highly independent from the variable positioning of the objects in the MRI scanner. This allows one to use the method to carry out follow-up examinations which are reliable, particularly follow-up examinations of the development of a disease with or without therapeutic treatment.

In other words, the present method allows one to identify the development, for example, of a disease, with or without a therapy treatment, which has occurred from an initial imaging session to successive sessions or ones carried out at different subsequent times.

Follow-up examinations provide a very important tool for analysing the development of a disease or the response to a therapy. Generally today, MRI is considered not to be useful for follow-up examinations due to the fact that it is not simple to position the body under examination exactly in the same position at each imaging session. This problem can be overcome by using the method according to the present invention.

Figure 5:
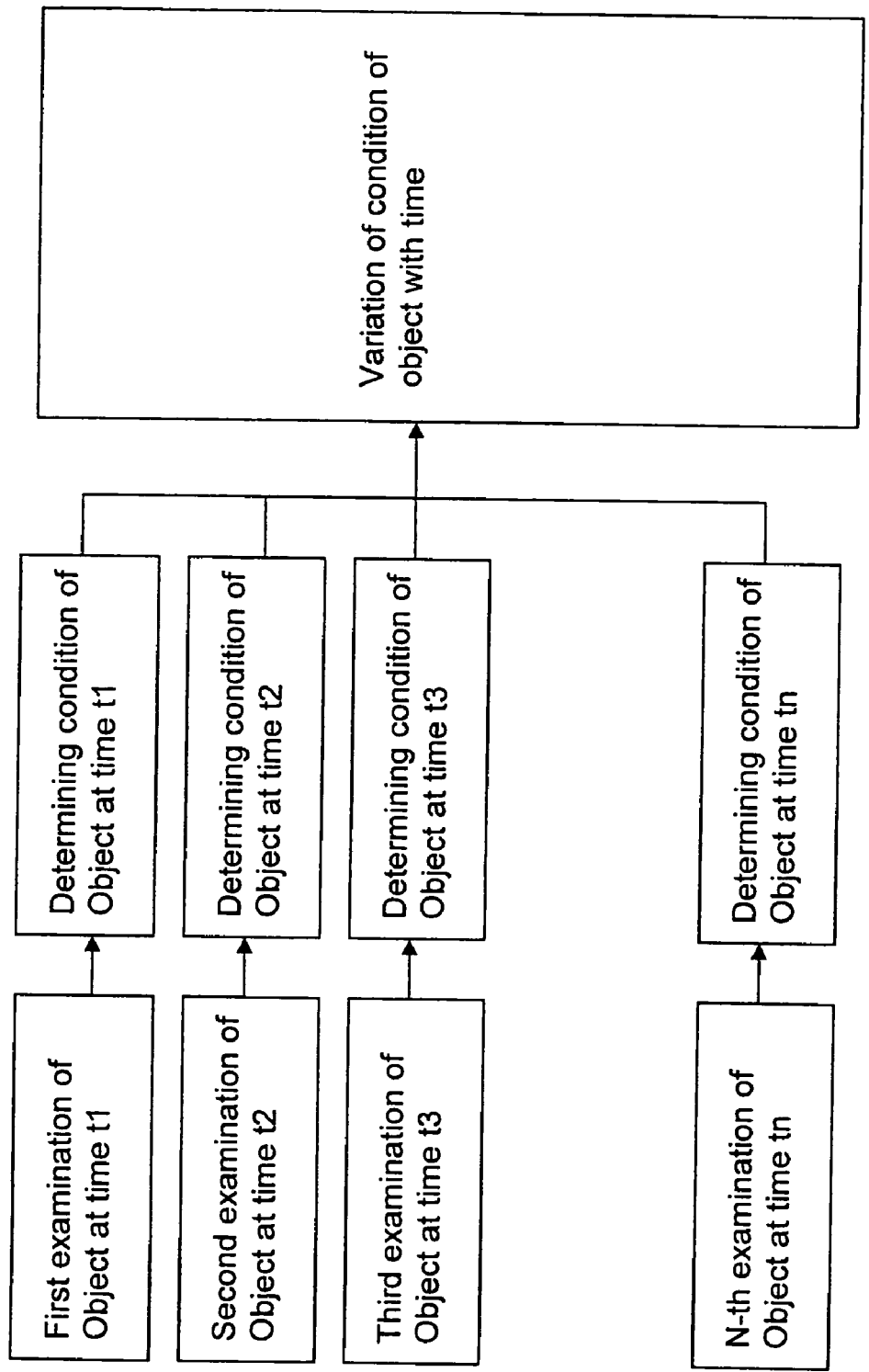
FIG. 5 illustrates a table explaining the basic steps of a disease follow-up according to the present invention; and, FIGS. 6 A to D illustrate an example of the use of markers in order to identify the same section plane along which the MRI image has to be acquired independently of the position of the object under examination in the MRI scanner, which in this case is a hand.

FIG. 5 illustrates the steps of a follow-up being carried out with the method according to the present invention.

The object to be examined is subjected to an imaging session as previously described at different times. At each time, the condition of the examined body is determined with the method described above either by comparing the condition with a database of data relative to sample objects or also by simply comparing the data of the previous imaging sessions. This allows one to reconstruct a development time table of the conditions of the object.

A particular application of the above-disclosed method for determining the condition of an object comprises determining the disease activity of rheumatisms and arthritis, particularly of rheumatoid arthritis. In this case, the object to be examined is the anatomical region of the wrist and the region of interest is the synovial membrane. Indeed, it is known that the synovial membrane is an anatomical site where inflammation can be detected at early stages. Thus the method according to the present invention can be used for determining the degree of rheumatoid arthritis activity and for carrying out a follow-up of a patient who is affected by rheumatoid arthritis. The database is generated by carrying out the MRI acquisition steps as described above, particularly using a three-dimensional MRI method. After one or more scout images are acquired, a region of interest centered at the synovial membrane is defined and confirmed by the user. Anatomical and/or external markers can be identified and or defined and also, or alternatively, external markers are placed on the hand at uniquely identifiable points of the morphology of the hand. The contrast media perfusion measurements are carried out for each patient having a known degree of activity of rheumatoid arthritis. For each patient, the same region of interest is selected by using the markers and the registration algorithm, thus ensuring that the region of interest is always identical and centered at the synovial membrane.

After having generated the database, a patient can be subjected to a perfusion measurement carried out in exactly the same manner as the perfusion measurements of the sample patients. The same region of interest is selected by using the anatomical and/or external markers and the registration algorithm. The user can also confirm the region of interest by visualizing the image on a screen and visually recognizing the synovial membrane. By means of a comparison method or a predictive algorithm, the degree of disease activity can then be determined for the patient.

The method allows one to determine if the disease is present or not and if the disease is active or not.

Furthermore, the patient can be submitted to a follow-up observation. At each imaging session for contrast means perfusion measurement, the same region of interest is selected by using the markers as described above and for each perfusion measurement the degree of disease activity can be determined. In this way the development of the disease can be controlled and if the patient is submitted to a therapy, the success of the therapy and the progress in the disease regression can be monitored, thus allowing one to have a very strict and precise control of the disease development and/or of the effectiveness of the therapy.

Obviously, the above method according to the invention either for determining the conditions of disease activity or for a disease follow-up can be applied to other kind of diseases, particularly to diseases which cause a variation in the vascularisation of the inflamed or attached tissue or tissues.

As for the method for determining the conditions of an object and for the method of follow-up according to the invention, the diagnostic field is not the only one in which the said method can be used, but it can be applied also to in vitro biological tissues or to non-biological material.

Referring to the example of a solid permeable body, variation of the condition relative to the permeation of a fluid such as a liquid or a gas within the solid body can be observed and determined, for example, depending on other parameters which may vary in time, such as temperature, relative humidity, or a condition induced by other physical or chemical treatments to which the body may be subjected.

What is claimed is:

1. A method for determining the condition of an object by MRI, comprising the steps of:
    a) acquiring an image by MRI of a sample object under examination at each of several different successive times within a predetermined time period, the sample object having at least one known condition;
    b) determining a mean intensity of an MRI signal for at least a portion of each said acquired image;
    c) constructing an empirical time dependency function by using data pairs consisting of each said mean intensity and a corresponding time of acquisition of said image;
    d) providing at least a second object to be examined having an unknown condition and carrying out the steps a) to c) using the said second object; and,
    e) comparing the empirical time dependency function relating to the sample object to the empirical time dependency function relating to the second object in order to assist in identifying the unknown condition of the second object.

2. The method according to claim 1 wherein the step of comparing comprises graphically representing the empirical time dependency function of the sample object and of the second object by drawing a curve passing through the points represented by each data pair for the sample object and for the second object.

3. The method according to claim 2 wherein the graphical representations of the functions approximating the empirical time dependency function relating to the sample object and to the second object are carried out manually.

4. The method according to claim 2 wherein the graphical representations of the functions approximating the empirical time dependency function relating to the sample object and to the second object are carried out by an approximation algorithm which determines a path of a curve passing through the points represented by each data pair consisting of the time of acquisition of the corresponding image and the mean intensity of said images.

5. The method according to claim 1 wherein both the sample object and the second object have a continuously varying condition, the steps a) to c) being carried out for the continuously varying condition.

6. The method according to claim 1 wherein steps a) to c) are repeated for each of several additional sample objects under examination, and wherein the empirical time dependency function relating to the second object is compared to the empirical time dependency functions relating to the sample objects and wherein the identification of the unknown condition of the second object is obtained by interpolation.

7. The method according to claim 6 wherein the step of comparing comprises graphically representing the empirical time dependency function of the sample objects and of the second object by drawing a curve passing through the points represented by each data pair for the sample objects and for the second object, and wherein the graphical representation of the empirical time dependency function of the second object falls at least partly or completely between the graphical representation of the empirical time dependency function of two sample objects.

8. The method according to claim 1 wherein said step of acquiring an image by MRI for the sample object and for the second object includes the use of a medium which is able to diffuse within the objects.

9. The method according to claim 1 wherein said step of acquiring an image by MRI for the sample object and for the second object includes acquiring a first panoramic or scout image.

10. The method according to claim 9 wherein said first panoramic or scout image is used to determine at least one selected section plane across the object, said images of step a) being acquired at several different successive times along said selected plane of said sample object and of said second object.

11. The method according to claim 1 wherein a first image along a first section plane is acquired for the sample object and for the second object and a region of interest of the said image is determined, a geometrical shape and position of said region of interest being determined and selected on each subsequent image acquired at later times along the same section plane.

12. The method according to claim 2 wherein step e) is performed visually.

13. The method according to claim 1 wherein said images are three-dimensional images.

14. The method according to claim 13 wherein a first three-dimensional image is acquired and a region of interest of the said three dimensional image is determined, a position in space and boundaries of the said region of interest being determined, the said region of interest being automatically selected for each of said several different successive times.

15. The method according to claim 1 wherein mean intensities are determined for at least two different regions of said images of the sample object and the second object and an empirical time dependency function of the mean intensity is constructed separately for each different region by using data pairs consisting of the mean intensity of the corresponding selected region and the corresponding time of acquisition.

16. The method according to claim 15 wherein an empirical time dependency function is constructed for each object using the sum of the mean intensities of the different regions.

17. The method according to claim 13, further comprising the steps of:
    defining within each said three-dimensional image at least one plane crossing a volume represented by said three-dimensional image; and,
    reconstructing the image along said at least one plane using data from said three-dimensional image by selecting data falling on said at least one plane crossing the volume.

18. The method according to claim 1 wherein markers are applied to the objects in uniquely defined positions thereof, the markers generating uniquely recognizable image data in the acquired images.

19. The method according to claim 18 wherein the markers are defined as selected regions of the objects which are uniquely identifiable in the images of selected section planes.

20. The method according to claim 1 wherein the objects consist of biological tissue.

21. The method according to claim 8 wherein the sample object is an anatomical region of a body under examination and wherein the second object is an anatomical region of another body under examination.

22. The method according to claim 21 wherein the medium applied to the object and permeating the object is a contrast agent supplied to the anatomical region of the body under examination.

23. The method according to claim 1 wherein the step of constructing an empirical time dependency function comprises analytically determining a parameter of a function approximating the said empirical time dependency function; and wherein the step of comparing the empirical time dependency functions comprises comparing the parameters of the function approximating the empirical time dependency function relating to the sample object and to the second object.

24. A method for carrying out a follow up of at least one pathological condition of biological tissue, comprising the steps of:
    a) acquiring at least one image by MRI along at least one slice or one section plane of a sample biological tissue, having a known condition, at different successive times within a predetermined time period;
    b) determining a mean intensity of an MRI signal for at least a region of each said acquired image, said region being generally the same for each image;
    c) constructing an empirical time dependency function by using data pairs consisting of each said mean intensity and a corresponding time of acquisition of said image;
    d) providing at least a second biological tissue to be examined having an unknown condition and carrying out the steps a) to c) using the said second biological tissue; and,
    e) comparing the empirical time dependency function relating to the sample biological tissue to the empirical time dependency function relating to the second biologic tissue in order to assist in identifying the unknown condition of the second biological tissue.

25. The method according to claim 24 wherein the step of comparing comprises graphically representing the empirical time dependency function of the sample biological tissue and of the second biological tissue by drawing a curve passing through the points represented by each data pair for the sample biological tissue and for the second biological tissue.

26. The method according to claim 25 wherein the graphical representations of the functions approximating the empirical time dependency function relating to the sample biological tissue and to the second biological tissue are carried out manually.

27. The method according to claim 24 wherein the graphical representations of the functions approximating the empirical time dependency function relating to the sample biological tissue and to the second biological tissue are carried out by an approximation algorithm which determines a path of a curve passing through the points represented by each data pair consisting of the time of acquisition of the corresponding image and the mean intensity of said images.

28. The method according to claim 24 wherein both the sample biological tissue and the second biological tissue have a continuously varying condition, the steps a) to c) being carried out for the continuously varying condition.

29. The method according to claim 24 wherein steps a) to c) are repeated for each of several additional sample biological tissues under examination, and wherein the empirical time dependency function relating to the second biological tissue is compared to the empirical time dependency functions relating to the sample biological tissues and wherein the identification of the unknown condition of the second biological tissue is obtained by interpolation.

30. The method according to claim 29 wherein the step of comparing comprises graphically representing the empirical time dependency function of the sample biological tissues and of the second biological tissue by drawing a curve passing through the points represented by each data pair for the sample biological tissues and for the second biological tissue, and wherein the graphical representation of the empirical time dependency function of the second biological tissue falls at least partly or completely between the graphical representation of the empirical time dependency function of two sample biological tissues.

31. The method according to claim 24 wherein said step of acquiring an image by MRI for the sample biological tissue and for the second biological tissue includes the use of a medium which is able to diffuse within the tissues.

32. The method according to claim 24 wherein said step of acquiring an image by MRI for the sample biological tissue and for the second biological tissue includes acquiring a first panoramic or scout image.

33. The method according to claim 32 wherein said first panoramic or scout image is used to determine at least one selected section plane across the tissue, said images of step a) being acquired at several different successive times along said selected plane of said sample biological tissue and of said second biological tissue.

34. The method according to claim 24 wherein a first image along a first section plane is acquired for the sample biological tissue and for the second biological tissue and a region of interest of the said image is determined, a geometrical shape and position of said region of interest being determined and selected on each subsequent image acquired at later times along the same section plane.

35. The method according to claim 25 wherein step e) is performed visually.

36. The method according to claim 24 wherein said images are three-dimensional images.

37. The method according to claim 36 wherein a first three-dimensional image is acquired and a region of interest of the said three dimensional image is determined, a position in space and boundaries of the said region of interest being determined, the said region of interest being automatically selected for each of said several different successive times.

38. The method according to claim 24 wherein mean intensities are determined for at least two different regions of said images of the sample biological tissue and the second biological tissue and an empirical time dependency function of the mean intensity is constructed separately for each different region by using data pairs consisting of the mean intensity of the corresponding selected region and the corresponding time of acquisition.

39. The method according to claim 38 wherein an empirical time dependency function is constructed for each tissue using the sum of the mean intensities of the different regions.

40. The method according to claim 36, further comprising the steps of:
defining within said three-dimensional images at least one plane crossing a volume represented by said three-dimensional image; and,
reconstructing the image along said at least one plane using data from said three-dimensional image by selecting data falling on said at least one plane crossing the volume.

41. The method according to claim 24 wherein markers are applied to the tissues in uniquely defined positions thereof, the markers generating uniquely recognizable image data in the acquired images.

42. The method according to claim 41 wherein the markers are defined as selected regions of the tissues which are uniquely identifiable in the images of selected section planes.

43. The method according to claim 24 wherein the sample biological tissue is an anatomical region of a body under examination and wherein the second biological tissue is an anatomical region of another body under examination.

44. The method according to claim 42 wherein the medium applied to the tissues and permeating the tissues is a contrast agent supplied to the anatomical region of the body under examination.

45. The method according to claim 24 wherein the step of constructing an empirical time dependency function comprises analytically determining a parameter of a function approximating the said empirical time dependency function; and
wherein the step of comparing the empirical time dependency functions comprises comparing the parameters of the function approximating the empirical time dependency function relating to the sample biological tissue and to the second biological tissue.

46. The method according to claim 24 wherein the pathological condition of the biological tissue is rheumatoid arthritis.

47. The method according to claim 40 wherein the pathological condition of the biological tissue is rheumatoid arthritis.

48. A method for carrying out a follow-up of disease activity of pathological conditions of an anatomical region of a body by contrast media perfusion measurements in the said anatomical region, comprising the steps of:
a) generating a database of perfusion curves, each one uniquely associated to a well defined degree of disease activity;
b) the said database being generated by acquiring at least one image of the anatomical region by MRI along at least one slice or one section plane of the anatomical region in patients or a three-dimensional MRI image of the anatomical region in patients having a known degree of disease activity;
c) acquiring for each patient having a well defined degree of disease activity, a sequence of MRI images, which sequence comprises a certain number of MRI images taken at different times within a certain period of time;
d) the said period starting immediately after or at the injection of a contrast medium in the anatomical region and terminating after a certain time determined as a typical duration of contrast media perfusion in the anatomical region;
e) determining for each image or for a selected region of each image, which selected region is identical for each image or refers to an identical part of the imaged anatomical region under examination the mean intensity of the image data acquired;
f) constructing an empirical time dependency function of the mean intensity by using the data pairs consisting of the mean intensity of each image or of the part of each image and the corresponding time of acquisition;
g) analytically determining the parameter of a function approximating the said empirical time dependency function;
h) determining the disease activity in the same anatomical region of a patient having an unknown level of disease activity by carrying out the steps of injecting the said contrast media in the anatomical region of the said patient and by acquiring a sequence of MRI images of the anatomical region for the predetermined period of time and finally constructing the empirical time dependency function of the mean intensity by using the data pairs consisting of the mean intensity of each image or of the part of each image and the corresponding time of acquisition and analytically determining the parameter of a function approximating the said empiric time dependency function; and,
i) comparing the parameters of the function approximating the empirical time dependency function relating to the database in order to detect the disease activity level.

49. The method according to claim 48 wherein a follow-up of the disease activity comprises the repetition at several different times of the steps h) and i) for determining changes in the disease activity degree in time and during a therapeutic treatment.

50. The method according to claim 49 wherein a first MRI scout image of the anatomical region is acquired before injection of the contrast media;
a region of interest is defined on said image comprising or containing the image of an anatomically relevant object;
the parameters of position and boundaries of the said region of interest are determined relative to the image acquired or relative to anatomical markers or to external markers previously defined;
the said region of interest being automatically determined for each MRI image of the sequence of MRI images and in each subsequent image acquisition of the follow-up method; and,
the mean intensity of the image data within the said region of interest being used as a time dependent perfusion measure at the time of acquisition of the corresponding image used to construct the time dependent perfusion function.

51. A method for carrying out a follow-up of disease activity of a pathological condition of an anatomical region of a body by contrast media perfusion measurements in the said anatomical region, comprising the steps of:
a) generating a database of perfusion curves, each one uniquely associated to a well defined degree of disease activity;
b) the said database being generated by acquiring at least one image of the anatomical region by MRI along at least one slice or one section plane of the anatomical region in patients or a three-dimensional MRI image of the anatomical region in patients having a known degree of disease activity;
c) for each patient having a well defined degree of disease activity, a sequence of MRI images is acquired which sequence comprises a certain number of MRI images taken at different times within a certain period of time;

d) the said period starting immediately after or at the injection of a contrast medium in the anatomical district and terminating after a certain time determined as a typical duration of contrast media perfusion in the anatomical region;

e) determining for each image or for a selected region of each image, which selected region is identical for each image or refers to an identical part of the imaged anatomical district under examination the mean intensity of the image data acquired;

f) constructing an empirical time dependency function of the mean intensity by using the data pairs consisting of the mean intensity of each image or of the part of each image and the corresponding time of acquisition;

g) graphically representing the function describing the said empirical time dependency by drawing a curve passing through the points represented by each data pair consisting of the time of acquisition of the corresponding image and the mean intensity of the said image;

h) determining the disease activity in the same anatomical region of a patient having an unknown level of disease activity by carrying out the steps of injecting the said contrast media in the anatomical region of the said patient and by acquiring the sequence of MRI images of the anatomical region for the predetermined period of time and finally constructing the empirical time dependency function of the mean intensity by using the data pairs consisting of the mean intensity of each image or of the part of each image and the corresponding time of acquisition and graphically representing the function describing the said empirical time dependency by drawing a curve passing through the points represented by each data pair consisting of the time of acquisition of the corresponding image and the mean intensity of the said image; and, i) visually comparing the graphical representations of the functions approximating the empirical time dependency function relating to the database in order to detect the disease activity level.

52. The method according to claim 51 wherein a follow-up of the disease activity comprises the repetition at several different times of the steps h) and i) for determining changes in the disease activity degree in time and during a therapeutic treatment.

53. The method according to claim 51 wherein a first MRI scout image of the anatomical region is acquired before injection of the contrast media;

a region of interest is defined on said image comprising or containing the image of an anatomically relevant object;

parameters of position and boundaries of the said region of interest are determined relative to the image acquired or relative to anatomical markers or to external markers previously defined;

the said region of interest being automatically determined for each MRI image of the sequence of MRI images and in each following image acquisition of the follow-up method; and, the mean intensity of the image data within the said region of interest being used as a time dependent perfusion measure at the time of acquisition of the corresponding image used to construct the time dependent perfusion function.

* * * * *